US011052256B2

United States Patent
Stahmann et al.

(10) Patent No.: US 11,052,256 B2
(45) Date of Patent: Jul. 6, 2021

(54) HOUSING FOR IMPLANTABLE MEDICAL DEVICE

(71) Applicant: Cardiac Pacemakers, Inc., St. Paul, MN (US)

(72) Inventors: Jeffrey E. Stahmann, Ramsey, MN (US); Keith R. Maile, New Brighton, MN (US); Moira B. Sweeney, St. Paul, MN (US)

(73) Assignee: Cardiac Pacemakers, Inc., Minnesota (MN)

( * ) Notice: Subject to any disclaimer, the term of this patent is extended or adjusted under 35 U.S.C. 154(b) by 115 days.

(21) Appl. No.: 16/224,333

(22) Filed: Dec. 18, 2018

(65) Prior Publication Data

US 2019/0184179 A1    Jun. 20, 2019

Related U.S. Application Data

(60) Provisional application No. 62/607,726, filed on Dec. 19, 2017.

(51) Int. Cl.
*A61N 1/37* (2006.01)
*H05K 9/00* (2006.01)
*A61N 1/375* (2006.01)
*A61N 1/08* (2006.01)
(Continued)

(52) U.S. Cl.
CPC ............. *A61N 1/3718* (2013.01); *A61N 1/05* (2013.01); *A61N 1/08* (2013.01); *A61N 1/375* (2013.01); *A61N 1/37223* (2013.01); *A61N 1/37512* (2017.08); *H05K 9/0022* (2013.01); *H05K 9/0083* (2013.01)

(58) Field of Classification Search
CPC ... A61N 7/02; A61N 2007/034; A61N 1/3718
See application file for complete search history.

(56) References Cited

U.S. PATENT DOCUMENTS

| 8,884,779 | B2 | 11/2014 | Herman et al. |
| 9,462,962 | B2 | 10/2016 | Doerr |
| 2002/0019658 | A1 | 2/2002 | Munshi |

(Continued)

FOREIGN PATENT DOCUMENTS

| WO | WO-2016111690 A1 | 7/2016 |
| WO | WO-2019126195 A1 | 6/2019 |

OTHER PUBLICATIONS

"International Application Serial No. PCT/US2018/066268, International Preliminary Report on Patentability dated Jul. 2, 2020", 8 pgs.

(Continued)

*Primary Examiner* — Michael J D Abreu
(74) *Attorney, Agent, or Firm* — Schwegman Lundberg & Woessner, P.A.

(57) ABSTRACT

An implantable medical device (IMD) includes a heterogeneous housing configured to receive and store one or more components of the IMD. The housing includes an intrinsically non-conductive and non-magnetic base material and at least one dopant with a property of at least one of electrical conductance and magnetic permeability. The base material and the dopant form a first region of the housing including a first skin depth and a second region of the housing including a second skin depth different than the first skin depth.

20 Claims, 6 Drawing Sheets

(51) Int. Cl.
*A61N 1/372* (2006.01)
*A61N 1/05* (2006.01)

(56) References Cited

U.S. PATENT DOCUMENTS

| | | | |
|---|---|---|---|
| 2005/0197677 A1* | 9/2005 | Stevenson | A61N 1/3754 |
| | | | 607/36 |
| 2005/0288743 A1* | 12/2005 | Ahn | A61N 1/3787 |
| | | | 607/61 |
| 2006/0137688 A1 | 6/2006 | Aisenbrey | |
| 2009/0228075 A1* | 9/2009 | Dion | H01Q 5/321 |
| | | | 607/60 |
| 2013/0197550 A1* | 8/2013 | Dietz | A61N 7/00 |
| | | | 606/169 |
| 2013/0289372 A1* | 10/2013 | Imran | A61B 5/1459 |
| | | | 600/339 |
| 2014/0058482 A1 | 2/2014 | Gupta et al. | |

OTHER PUBLICATIONS

"International Application Serial No. PCT/US2018/066268, International Search Report dated Apr. 3, 2019", 5 pgs.
"International Application Serial No. PCT/US2018/066268, Written Opinion dated Apr. 3, 2019", 6 pgs.

* cited by examiner

HOUSING FOR IMPLANTABLE MEDICAL DEVICE

CLAIM OF PRIORITY

This application claims the benefit of priority under 35 U.S.C. § 119(e) of U.S. Provisional Patent Application Ser. No. 62/607,726, filed on Dec. 19, 2017, which is herein incorporated by reference in its entirety.

BACKGROUND

Implantable medical devices (IMDs), such as implantable cardioverter defibrillator (ICD) or cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

IMDs also include a number of other types of devices including drug infusion pumps, sensors, neurostimulators, among a variety of other devices designed to be implanted and to treat or support treatment of various medical conditions. IMDs commonly include a housing made of a biologically compatible material and are often constructed from a biologically compatible metal like titanium.

SUMMARY

The present disclosure is directed to, inter alia, implantable medical devices including and methods of making heterogeneous housings with a non-uniform distribution of one or more characteristics or properties, including, for example, a non-uniform skin depth in different regions or portions thereof.

Example 1 is an implantable medical device (IMD) comprising: one or more electrical components; and a heterogeneous housing containing the one or more components of the IMD, the housing comprising: an intrinsically non-conductive and non-magnetic base material; and at least one dopant comprising at least one of electrical conductance and magnetic permeability, the base material and the dopant forming a first region of the housing having a first skin depth and a second region of the housing having a second skin depth different than the first skin depth.

In Example 2, the subject matter of Example 1 optionally includes wherein the base material is selected from the group consisting of polymers, ceramics, glasses, composites, metamaterials and combinations thereof.

In Example 3, the subject matter of Example 1 optionally includes wherein one of the first and second skin depths is approximately 10 mm at an operational frequency of the IMD.

In Example 4, the subject matter of Example 1 optionally includes wherein one of the first and second skin depths is approximately 1 mm at an operational frequency of the IMD.

In Example 5, the subject matter of Example 1 optionally includes wherein one of the first or the second skin depth is approximately 0.1 mm at an operational frequency of the IMD.

In Example 6, the subject matter of Example 1 optionally includes wherein one of the first and second regions of the housing propagates electromagnetic communication signals and attenuates electromagnetic noise signals.

In Example 7, the subject matter of Example 1 optionally includes wherein one of the first and second regions of the housing propagates desired electromagnetic energy and attenuates undesired electromagnetic energy.

In Example 8, the subject matter of Example 1 optionally includes wherein the dopant has a target conductance and a target magnetic permeability that locally increase magnetic induction and skin depth of one of the first and second regions of the housing including the dopant relative to one or more other regions of the housing.

In Example 9, the subject matter of Example 1 optionally includes wherein the base material is conformal to a structure and/or component within the housing.

In Example 10, the subject matter of Example 1 optionally includes wherein the housing is configured to be operatively coupled to one or more leads.

In Example 11, the subject matter of Example 1 optionally includes wherein the housing has one or more low impedance paths between an internal component and an external lead port.

In Example 12, the subject matter of Example 11 optionally includes wherein the one or more low impedance paths comprise one or more feedthroughs.

In Example 13, the subject matter of Example 1 optionally includes wherein the housing is rigid.

In Example 14, the subject matter of Example 1 optionally includes wherein the housing is flexible.

In Example 15, the subject matter of Example 1 optionally includes wherein at least one of the first and second regions comprises a rigid region and the other of the at lease one of the first and second regions comprises a flexible region.

In Example 16, the subject matter of Example 1 optionally includes wherein the dopant has a magnetism property and wherein the magnetism property comprises at least one of ferromagnetism, ferrimagnetism and anti-ferromagnetism.

In Example 17, the subject matter of Example 1 optionally includes wherein the one or more components comprise at least one of an antenna and another electrical component and the first and second regions are configured to selectively attenuate electromagnetic waves to the another electrical component or selectively propagate electromagnetic waves to the antenna.

In Example 18, the subject matter of Example 1 optionally includes wherein the first skin depth is greater than the second skin depth, the IMD further comprising an antenna disposed within the housing, and wherein the first region of the housing is arranged proximate the antenna to support propagation of electromagnetic waves to or from the antenna.

In Example 19, the subject matter of Example 1 optionally includes wherein the second skin depth is less than the first skin depth, the IMD further comprising a circuit board comprising two major surfaces, and wherein the second region of the housing is arranged in a path of electromagnetic waves normal to the major surfaces of the circuit boards, wherein the second region attenuates propagation of electromagnetic noise to the circuit board.

In Example 20, the subject matter of Example 1 optionally includes wherein the housing comprises a cylindrical housing with an elongated annular region and capped end regions.

In Example 21, the subject matter of Example 20 optionally includes wherein the first region comprises the elongated annular region and the second region comprises the capped end regions.

In Example 22, the subject matter of Example 21 optionally includes further comprising an antenna and a circuit board comprising two major surfaces disposed within the housing, and wherein: the first region of the housing is arranged in a path of electromagnetic waves received by and/or transmitted by the antenna; the second region of the housing is arranged in a path of electromagnetic waves normal to the major surfaces of the circuit boards; and the first skin depth is greater than the second skin depth.

In Example 23, the subject matter of Example 21 optionally includes further comprising an antenna and a circuit board comprising two major surfaces disposed within the housing, and wherein: the first region of the housing is arranged in a path of electromagnetic waves normal to the major surfaces of the circuit boards; the second region of the housing is arranged in a path of electromagnetic waves received by and/or transmitted by the antenna; and the first skin depth is less than the second skin depth.

Example 24 is a method of making a heterogeneous housing of an implantable medical device (IMD), the method comprising: forming the housing of the IMD from an intrinsically non-conductive and non-magnetic base material and at least one dopant; and varying the amount of dopant at first and second regions of the housing, the first region of the housing having a first skin depth and the second region of the housing having a second skin depth that is different than the first skin depth.

In Example 25, the subject matter of Example 24 optionally includes wherein the dopant property includes at least one of electrical conductance and magnetic permeability, wherein varied electrical conductance or magnetic permeability in the first and second regions of the housing creates different skin depths at the first and second regions.

In Example 25, the subject matter of Example 24 optionally includes wherein the first skin depth is larger than the second skin depth and the first region is configured to be proximate an antenna component to support propagation of signals to or from the antenna component.

In Example 26, the subject matter of Example 24 optionally includes wherein the second skin depth is less than the first skin depth and the second region is configured to be proximate a circuit board in the housing to attenuate signal transmission to the circuit board.

Example 27 is a housing for an implantable medical device (IMD), the housing comprising: an enclosure configured to receive and store one or more components of the IMD, the enclosure comprising: an intrinsically non-conductive and non-magnetic base material; at least one dopant that affects a regional skin depth of the enclosure; a first region having a first amount of dopant; and a second region having a second amount of dopant.

Example 28 is an implantable medical device (IMD) comprising: one or more electrical components; and a heterogeneous housing containing the one or more components of the IMD, the housing comprising: a base material having an intrinsic skin depth; and at least one dopant having at least one of electrical conductance and magnetic permeability, the base material and the dopant forming a first region of the housing having a first skin depth that is different than the intrinsic skin depth.

Example 29 is a method of making a heterogeneous housing of an implantable medical device (IMD), the method comprising: forming the housing of the IMD from a base material having an intrinsic skin depth and at least one dopant having at least one of electrical conductance and magnetic permeability; and varying the amount of dopant at a first region of the housing, the first region of the housing having a first skin depth that is different than the intrinsic skin depth.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Commonly used metallic IMD housings have a number of desirable characteristics. For example, metallic housings can be mechanically robust, providing rigidity and puncture resistance. Metallic IMD housings like titanium housings are biocompatible, relatively easily sterilized, and provide electromagnetic interference (EMI) shielding. However, some currently used housings may also have characteristics or properties that are undesirable including, for example, high conductivity. Such housings may also be homogenous with characteristics and/or properties that cannot be easily configured for different regions of the housing. A flexible housing (versus one that is rigid) may be advantageous or required to enable delivery/implantation of the device by allowing the device to conform to patient anatomy. Metallic housings may also complicate or constrain available options for manufacturing the IMD. Additionally, commonly used housings may be non-conformal requiring control of gases inside the housing including, for example, controlling gaseous water and/or hydrogen.

One characteristic of currently used metallic housings is high conductivity. Highly conductive and/or ferrous materials exhibit a number of properties/characteristics related to the manner in which the material affects energy waves transmitted therethrough. For example, highly conductive materials have a short skin depth. One effect or property of conductors is referred to as the skin effect. The skin effect is the tendency of an alternating electric current to be distributed within a conductor such that the current density is largest near the surface of the conductor, and decreases with greater depths into the conductor. The electric current flows mainly at the "skin" of the conductor, between the outer surface and a level called the skin depth. The skin effect causes the effective resistance of the conductor to increase at higher frequencies where the skin depth is smaller, thus reducing the effective cross-section of the conductor. Varying the skin depth of a conductor can have the effect of modulating the transparency/opaqueness of the conductor to different electromagnetic waves/signals.

The inventors have recognized, inter alia, that a heterogeneous IMD housing can be formed with regions that have different skin depths (and, in some cases, different other properties and/or characteristics) to provide different electromagnetic properties at regions of the housing. For example, a housing may be "tuned" to modulate the capacity (e.g., capability or amount) to transmit electromagnetic energy through different regions of the housing. For example, a first region of the housing may shield or be relatively opaque to energy transmission therethrough to protect components in that region within the housing from EMI. A second region of the housing, on the other hand, may be relatively transparent to and thereby allow transmission of energy therethrough to allow, for example, an inductive coil or (other energy receiver) to receive electromagnetic energy through the second region of the housing for recharging a battery within the housing. In another example, a first region of the housing may shield or be relatively opaque to energy transmission therethrough to protect components in that region within the housing from EMI, and a second region of the housing may be relatively transparent to and thereby allow transmission of energy therethrough to allow a communication antenna to be placed within the housing of the IMD versus within a non-conductive header of the IMD.

In one example in accordance with this disclosure, an IMD includes a heterogeneous housing configured to receive and store one or more components of the IMD. The housing may include an intrinsically non-conductive and non-magnetic base material and at least one dopant with a property of at least one of electrical conductance and magnetic permeability. The base material and the dopant form at least a first region of the housing comprising a first skin depth and a second region of the housing comprising a second skin depth different than the first skin depth.

The housing may, for example, include a conducting polymer. The conducting polymer may be either an electronically conducting polymer or an ionically conducting polymer. Electronically conducting polymers include conjugated conducting polymers and non-conductive polymers doped with a conductive material and/or a material with a large relative magnetic permeability (i.e. a ferromagnetic or ferrimagnetic material). The base material may, for example, be a polymer, for example, polyurethane, polyetheretherketone (PEEK) or styrene-b-ethylene/butylene-b-styrene (SEBS), polyisobutylene polyurethane, or an epoxy, ceramic, glass, composite, metamaterial or any combination thereof that is structurally stable and biocompatible. The dopant may include any conductive and/or magnetic particle or substance that can be impregnated or otherwise mixed with the base material, including, for example, iron oxide (Fe3O4) nanoparticles, carbon nanotubes, carbon fibers, copper particles, copper fiber, iron particles, nickel particles, silver particles, alloys containing iron, nickel and/or cobalt, and metal plated particles.

In one example, the first skin depth is shorter than the second skin depth. In this example, a first component that is negatively affected by EMI, such as a printed circuit board (PCB) (or other circuit board), can be disposed within the housing adjacent the first region of the housing including the first skin depth and a second component configured to transmit and/or receive electromagnetic signals like an antenna can be disposed within the housing adjacent the second region including the second skin depth.

In one example, an IMD includes one or more electrical components and a heterogeneous housing containing the electrical component(s) of the IMD. The housing includes a base material with an intrinsic skin depth and at least one dopant having at least one of electrical conductance and magnetic permeability. The base material and the dopant form a first region of the housing having a first skin depth different than the intrinsic skin depth.

Some examples of this disclosure include an IMD housing including an intrinsically non-conductive and non-magnetic base material. As used in this disclosure, a material that is intrinsically non-conductive and non-magnetic includes materials with low but not necessarily zero conductance and magnetism. Such materials with low but not necessarily zero conductance and magnetism generally would not be selected for the ability such materials to interact with electromagnetic signals.

As used in this disclosure, a homogeneous material is a material that is substantially uniform in composition and/or character, for example, substantially uniform in color, weight, and mechanical, electrical, and/or other properties and/or characteristics. Conversely, a heterogeneous material is one that is distinctly non-uniform in such qualities.

Figure 1:
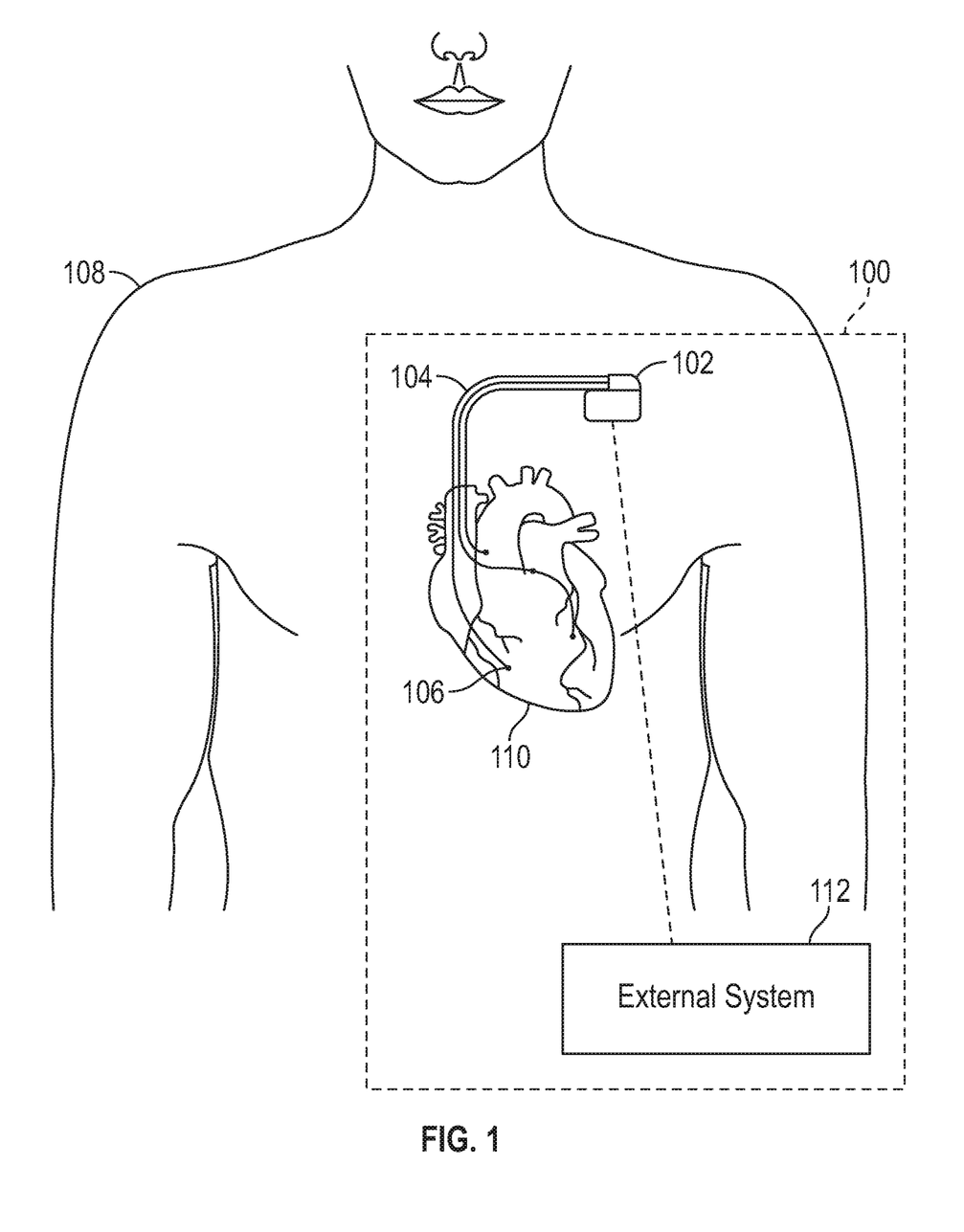
FIG. 1 depicts a system including an example implantable medical device in accordance with this disclosure.

FIG. 1 illustrates an example system 100 including an example IMD 102. IMD 102 can include a cardiac pacing device (i.e. pacemaker), cardiac resynchronization therapy (CRT) device, monitoring or sensory device that can optionally deliver therapy, neurostimulation device, leadless pacemaker, or other device. As shown in the example of FIG. 1, IMD 102 can include a cardiac device that is configured to deliver a pacing pulse (e.g., a pacemaker ICD with pacing capability or CRT device). IMD 102 can be coupled to at least one lead 104. The lead 104 can include an electrical conductor, such as a wire. An electrode 106 can be positioned on the lead 104, such as at a distal end of the lead 104. The lead 104 can deliver electrical pulses from IMD 102 to the electrode 106. The electrical pulses can be delivered to a patient 108 for stimulation therapy.

For instance, IMD 102 can deliver the electrical pulses to a heart 110 of the patient 108 to provide stimulation therapy, such as pacing, CRT, defibrillation, or the like. In an example, the electrode 106 can be located in the heart 108, such as in the right atrium, right ventricle, left ventricle, left atrium, or other location in or on the heart 108. IMD 102 can be communicatively coupled to an external device or system 112, such as a clinician programmer or patient communicator. The external system 112 can transmit therapy parameters to IMD 102 or receive sensory data collected by IMD 102. The external system 112 can, for example, facilitate programming of IMD 102. Alternatively or additionally, the external system 112 can wirelessly transmit electrical power to IMD 102 to recharge a battery disposed within the housing of the IMD.

Example IMD 102 of system 100 includes a heterogeneous housing configured to receive and store one or more components of the IMD. The housing of IMD 102 includes an intrinsically non-conductive and non-magnetic base material and at least one dopant with a property of at least one of electrical conductance and ferromagnetism. The housing includes at least a first region comprising a first skin depth and a second region comprising a second skin depth different than the first skin depth. In an example, the housing of IMD 102 includes base material with an intrinsic skin depth and at least one dopant having at least one of electrical conductance and magnetic permeability. The base material and the dopant form a first region of the housing of IMD 102 having a first skin depth that is different than the intrinsic skin depth of the base material. In one example, one of the first and second skin depths is in a range from approximately 0.1 millimeters (mm) to approximately 10 mm at an operational frequency of the IMD. In one example, one of the first and second skin depths is approximately 10 mm at an operational frequency of the IMD. In one example, one of the first and second skin depths is approximately 1 mm at an operational frequency of the IMD. In one example, one of the first and second skin depths is approximately 0.1 mm at an operational frequency of the IMD.

Figure 2:
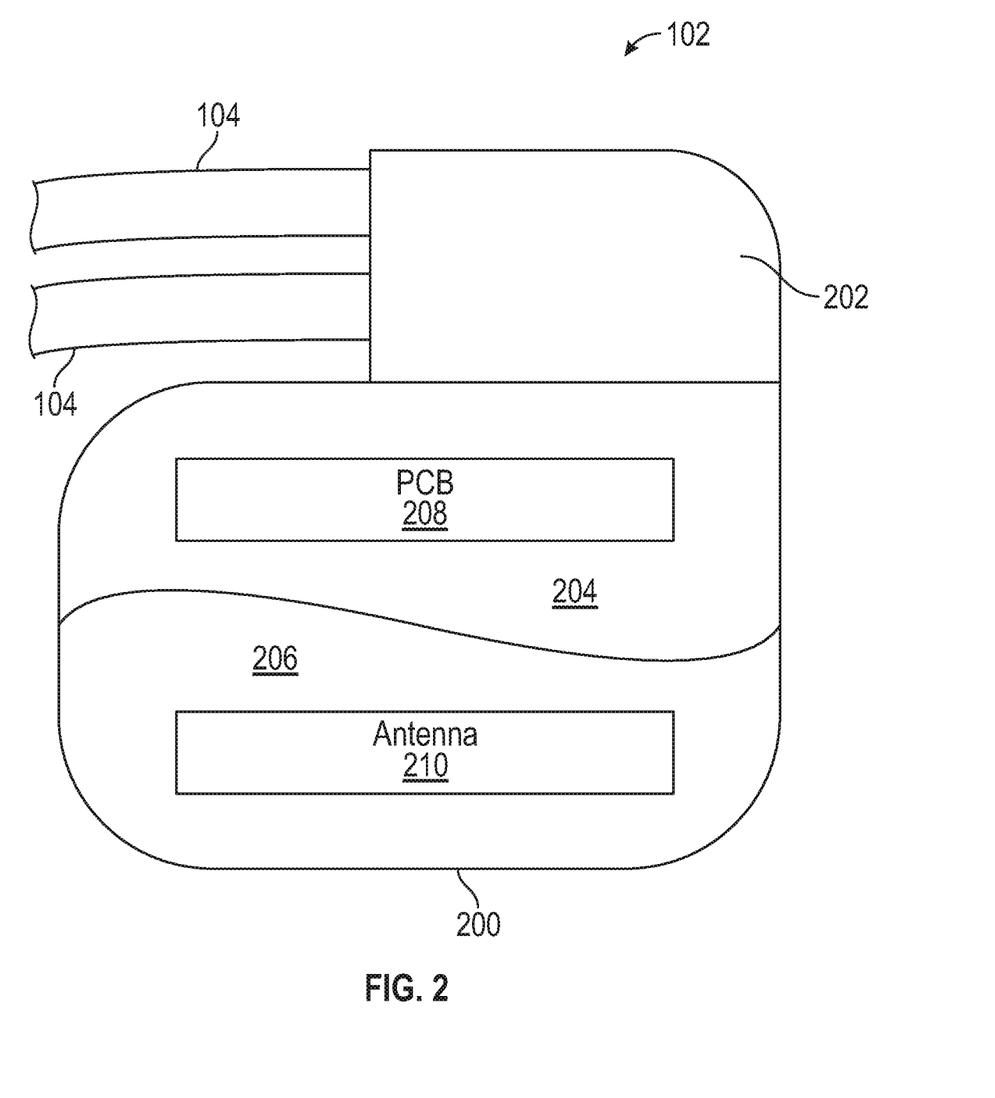
FIG. 2 depicts additional details of the example implantable medical device of FIG. 1.

FIG. 2 depicts an example of IMD 102 of system 100 of FIG. 1 in greater detail. In FIG. 2, IMD 102 includes housing 200 and header 202. Leads 104 are coupled to IMD 102 at header 202. Header 202 is connected to housing 200 and may include a number of mechanical and electrical connections to connect leads 104 and/or conductors thereof through and into components within housing 200. Housing 200 is includes multiple regions, which in the example of FIG. 2, include first region 204 and second region 206. PCB 208 is disposed within housing 200 adjacent first region 204. Antenna 210 is disposed within housing 200 adjacent second region 206.

PCB 208 could include a number of components and functions and, in some examples, is a single board with multiple chip sets or other components coupled thereto, or, in other examples, is a number of different boards including processors, sensors, pulse generators, etc. In other examples, an IMD can include circuit boards other than PCBs. In one example, PCB 208 includes sensing circuitry that is configured to detect physiological characteristics of the patient. PCB 208 may also include a controller that can receive signals from the sensing circuitry and, based on such signals, detect a cardiac event or physiologic condition. The controller of PCB 208 can be configured to initiate the delivery of electrical pulses based on a variety of factors, including, for example, pacing timing interval (a time interval between electrical pulses of the stimulation therapy), a detected cardiac event, or both in accordance with a programmed mode. PCB 208 can also include pulse generation circuitry that produces electrical pulse(s) for delivery to the patient via leads 104.

Antenna 210 can be structured in a variety of ways and can provide a number of functions useful to and/or required for the operation of IMD 102. For example, antenna 210 can transmit data and/or other information, including raw sensor signals, from IMD 102 to external device 112. Additionally, antenna 210 can receive data and other information from a device outside of the body of the patient, for example, external device 112, and can use the received information to control, improve, or otherwise affect the operation of IMD 102.

For example, antenna 210 can enable a clinician to transmit one or more programs that, when executed by a controller/processor of IMD 102, cause IMD 102 to deliver stimulation to the patient according to one or more stimulation parameters included in the program. Antenna 210 can also receive wireless power from an external charging device, which power received by antenna 210 can be used to recharge a battery of IMD 102. Antenna 210 can be a coiled, serpentine, spiral, or another type of antenna appropriate for use in example IMD 102.

Example IMD 102 or other IMDs in accordance with this disclosure can include additional and/or different components than PCB 208 and antenna 210 within the housing (200) of the IMD. Thus, the example of PCB 208 and antenna 210 is merely illustrative of the general example of having a first component that can be negatively affected by energy signals transmitted through housing 200, in this example, PCB 208, and a second component that requires or depends upon energy signals transmitted through housing 200 for its operation, in this example, antenna 210.

Housing 200 of IMD 102 is an enclosure that is configured to receive and store components of the implantable device, illustrated examples of which include PCB 208 and antenna 210. Housing 200 is heterogeneous, which means that the material from which the housing is formed is not homogenous and therefore varies in composition and/or properties in different portions/regions of the structure. Housing 200 includes an intrinsically non-conductive and non-magnetic base material and at least one dopant comprising at least one of electrical conductance and magnetism. The heterogeneously combined base material and dopant cause housing 200 to include first region 204 having a first skin depth and second region 206 having a second skin depth that is different than the first skin depth. In an example, housing 200 (and other IMD housings in accordance with this disclosure) can include a base material having an intrinsic skin depth and at least one dopant having at least one of electrical conductance and magnetic permeability. The base material and the dopant form a first region of housing 200 having a first skin depth that is different than the intrinsic skin depth of the base material.

As noted above, PCB 208 is disposed within housing 200 adjacent first region 204, and antenna 210 is disposed within housing 200 adjacent second region 206. First region 204, adjacent to which PCB 208 is arranged, has a first skin depth. Second region 204, adjacent to which antenna 210 is arranged, has a second skin depth that is different than the first skin depth of first region 206. As such, energy transmission will be affected differently through first region 204 and impinging upon adjacent PCB 208 than through second region 206 and impinging upon adjacent antenna 210. Modulating the characteristics and/or properties of the housing of an IMD in this manner can have a number of applications and associated benefits and/or advantages.

As an example, second region 206 of heterogeneous housing 200 may include a second skin depth that causes second region 206 to be more transparent to electromagnetic waves relative to an IMD housing with a homogeneous metallic housing. For example, the combination of base material and at least one dopant that produces the second skin depth of second region 206 may be selected to cause second region 206 to be transparent to a larger band of electromagnetic wave frequencies. It may be desirable and/or advantageous to receive and transmit a variety of frequencies using antenna 210 of IMD 102. As such, in an example, second skin depth of second region 206 may allow antenna 210 to receive and transmit communications and/or power at frequencies included in the Medical Implant Communication Service (MICS) band and at frequencies in the Bluetooth band.

In addition to or in lieu of tuning the second skin depth of second region 206, first region 204 of heterogeneous housing 200 may include a first skin depth that is different than the second skin depth and that causes first region 204 to be more opaque to electromagnetic waves relative to an IMD housing with a homogeneous metallic housing. For example, the combination of base material and at least one dopant that produces the first skin depth of first region 204 may be selected to cause first region 204 to be opaque to EMI signals that may interfere with the operation of PCB 208.

Figure 3:
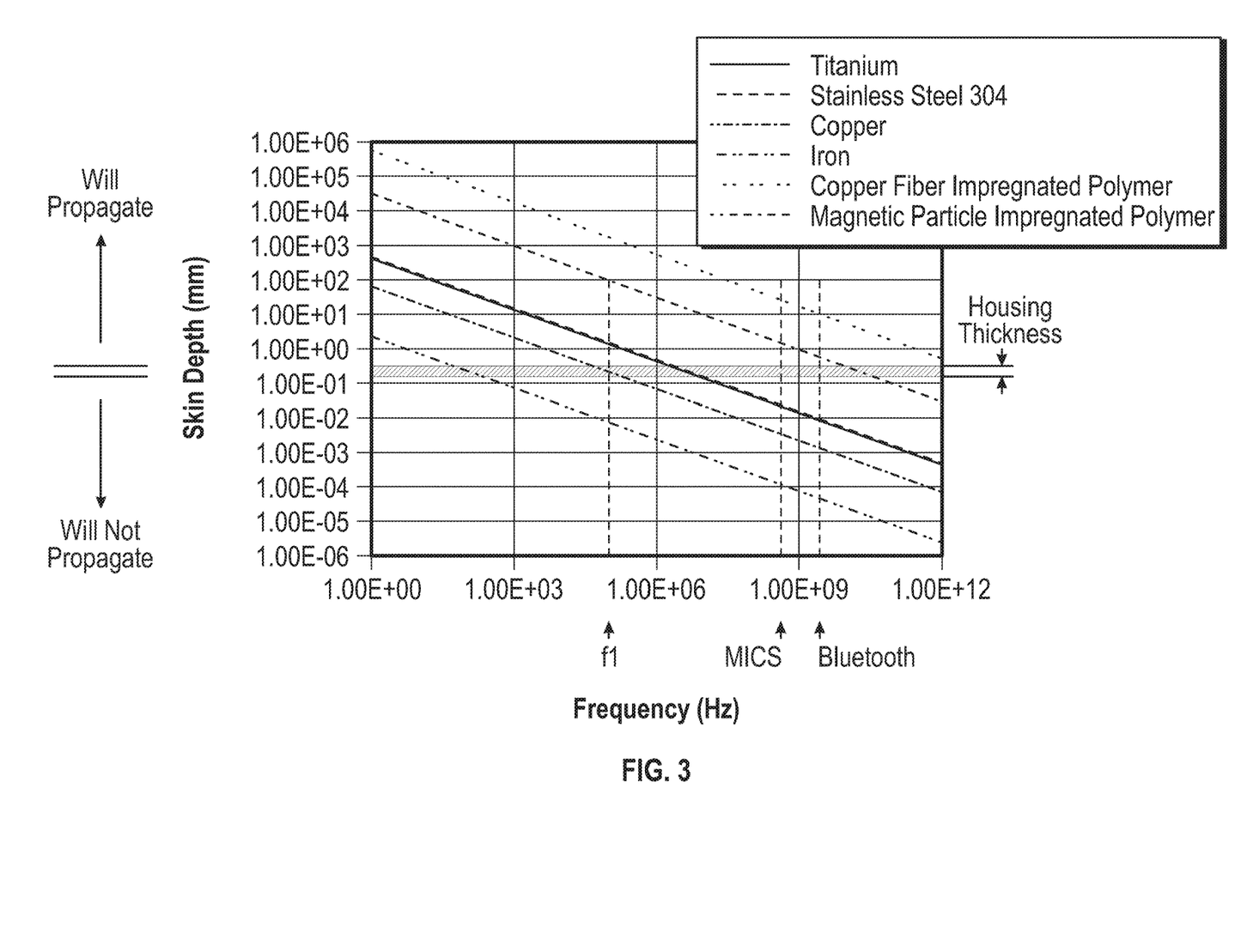
FIG. 3 is a graph of skin depth as a function of different operational frequencies of an IMD for a number of different IMD housing materials.

FIG. 3 is a graph of the skin depth as a function of different operational frequencies of an IMD for a number of different IMD housing materials. FIG. 3 depicts a number of different example materials forming the IMD, including metals titanium, stainless steel 304, copper, and iron. FIG. 3 also depicts the skin depth as a function of frequency for two example composite or heterogeneous IMD housings including copper fiber impregnated polymer and magnetic particle impregnated polymer. The data represented in the graph of FIG. 3 was generated based on an analytical (versus empirical) model of housing material skin depths at a range of operational frequencies relevant to IMDs.

As depicted in FIG. 3, for a given operational frequency of an IMD, the housing will or will not propagate electromagnetic waves therethrough depending upon the skin depth of the material of the housing. As an example, titanium, stainless steel 304, copper, and iron (for example, homogeneous housings of this material or an alloy thereof) will not propagate electromagnetic waves at the frequency of either MICs or Bluetooth. The composite or heterogeneous IMD housing materials of copper fiber impregnated polymer and magnetic particle impregnated polymer have substantially greater skin depth than the homogeneous metallic housings and may be configured to propagate both MICs and Bluetooth signals. An example of the practical outcome of the properties of IMD housings illustrated by the graph of FIG. 3 is that commonly used homogeneous metal housings like titanium may prevent use of antennas within the housing above certain frequencies, e.g., in the case of titanium, above 1 MHz. However, a heterogeneous IMD housing in accordance with examples of this disclosure may allow use of an antenna within the housing over a substantially broader range of frequencies and may enable communications/energy transmission at frequencies within the Bluetooth range, as an example.

Figure 4:
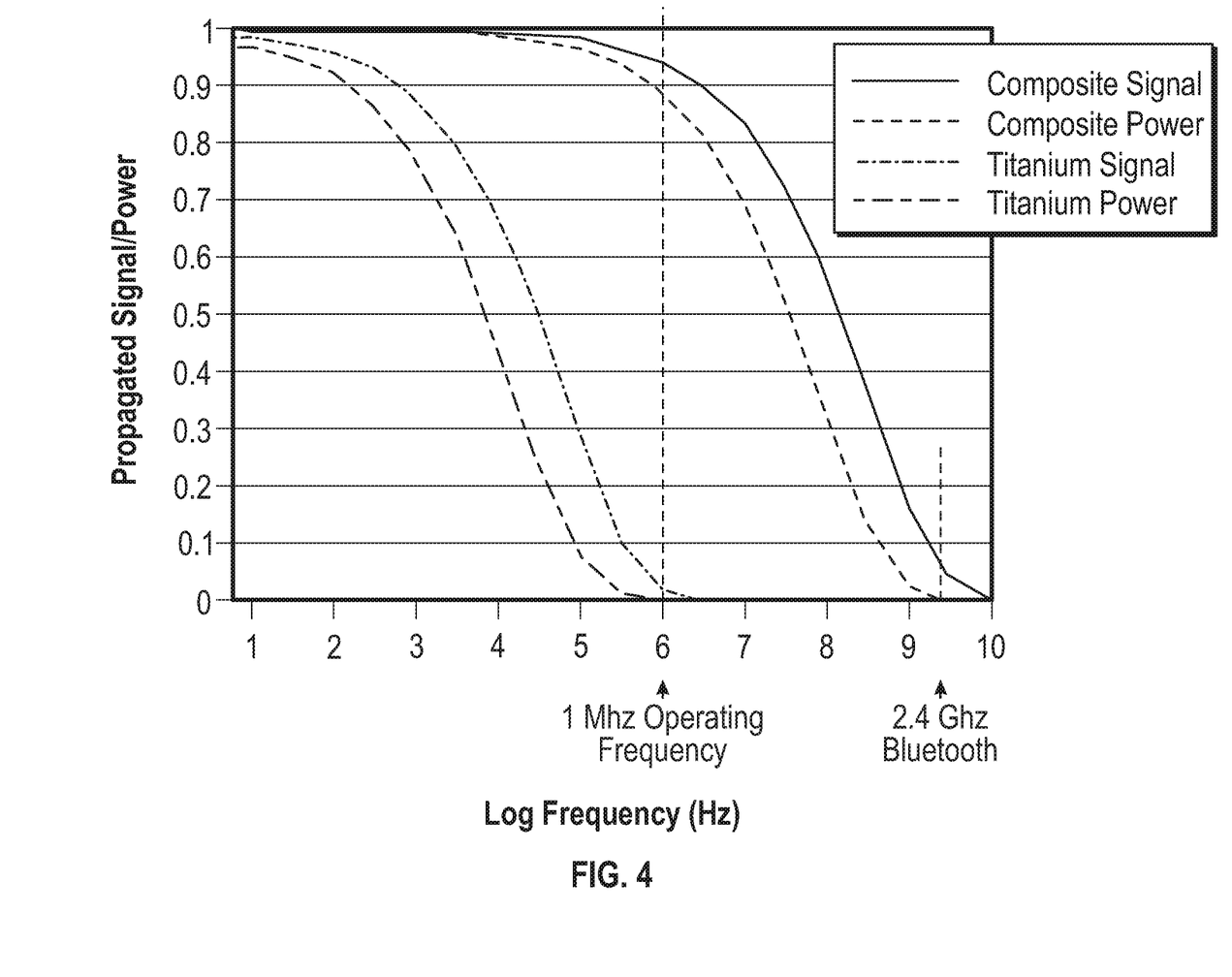
FIG. 4 is a graph of electromagnetic energy transmission or propagation through an IMD housing as a function of different operational frequencies, which are on a logarithmic scale.

FIG. 4 is a graph of electromagnetic energy transmission or propagation through an IMD housing as a function of different operational frequencies, which are on a logarithmic scale. FIG. 4 depicts two example housing materials, including titanium, or an example of a homogeneous metallic housing, and a composite, or an example heterogeneous IMD housing in accordance with this disclosure. For each of the example materials, titanium and the example composite, the graph of FIG. 4 depicts the propagation of a data signal and propagation of power through the material at different frequencies. Notably, the titanium IMD housing has relatively low signal and power propagation at an IMD operating frequency of 1 MHz and has no (or less than an effective threshold) propagation of signal and power at an IMD frequency in the Bluetooth spectrum. The following TABLES 1 and 2 include values for propagation of data signals and power for the example composite and titanium associated with the graph of FIG. 4.

TABLE 1

| At 1 MHz Operating Frequency | | | |
|---|---|---|---|
| Composite | | Titanium | |
| Signal | Power | Signal | Power |
| 0.94 | 0.89 | .018 | .00032 |

TABLE 2

| At 2.4 GHz Operating Frequency (Bluetooth) | | | |
|---|---|---|---|
| Composite | | Titanium | |
| Signal | Power | Signal | Power |
| 0.059 | 0.0035 | .00000 | .00000 |

The data and graphs of FIGS. 3 and 4 are provided to illustrate, inter alia, that an IMD housing can be tuned by varying the skin depth of the housing in different regions thereof in order to propagate desired electromagnetic energy but attenuate undesirable electromagnetic energy. As another example application of the effects/properties illustrated by FIGS. 3 and 4, an IMD housing can be tuned by varying the skin depth of the housing in different regions thereof in order to propagate energy waves in a first region of the housing and attenuate or effectively block energy waves from transmitting through a second region of the housing.

Figure 5:
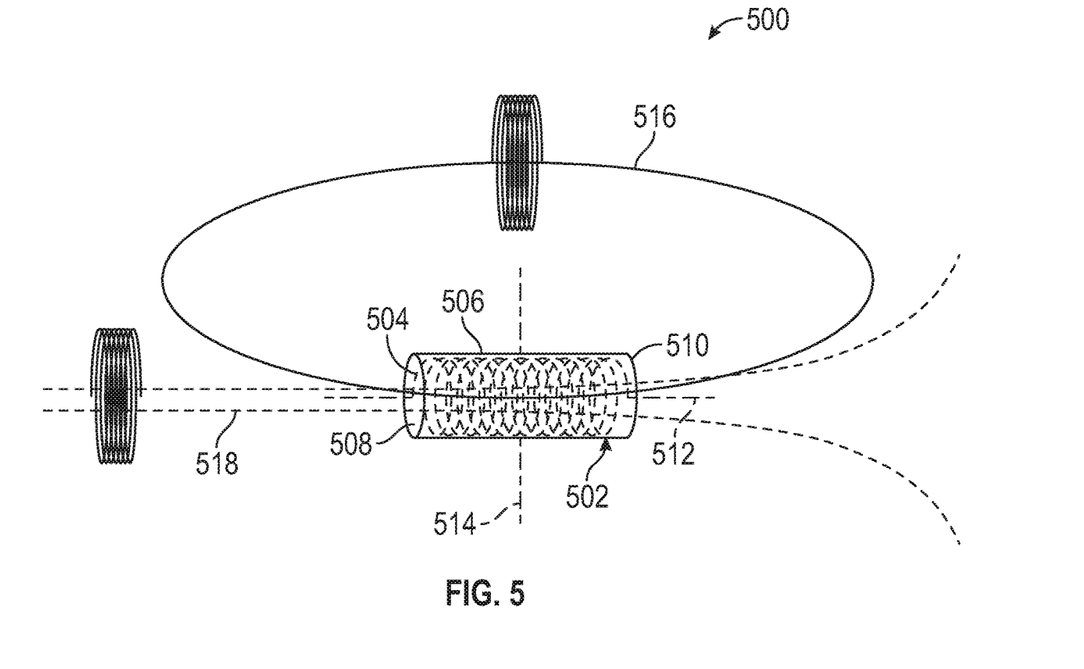
FIG. 5 depicts an example IMD including a heterogeneous housing with a non-uniform skin depth in different regions/portions thereof.

FIG. 5 depicts an example IMD 500 including heterogeneous housing 502 with a non-uniform skin depth in different regions/portions thereof. IMD 500 can include a number of different types of devices and can include various components, including processor/controller circuit board(s), battery and capacitor, antenna(s), among other examples. In FIG. 5, IMD 500 includes coiled antenna 504 stored within housing 502. Housing 502 is an elongated annular enclosure 506 with capped ends 508 and 510. Housing 502 can be a single integral structure or can include separately made and coupled components/sections.

Antenna 504 is arranged such that a longitudinal axis 512 of antenna 504 is generally aligned with the long axis of housing 502. Additionally, coiled antenna 504 extends across the length of housing 502 and the outer periphery of antenna 504 is concentric with or circumferentially aligned in some manner with annular portion 506 of housing 502. Axis 514 is one axis that is normal to annular portion 506 of housing 502 and to the windings of antenna 504. Field 516 schematically depicts the coradial magnetic field of antenna 504 and field 518 schematically depicts the coaxial magnetic field of the antenna.

IMD 500 includes heterogeneous housing 502. In examples, housing 502 comprises an intrinsically non-conductive and non-magnetic base material and at least one dopant comprising at least one of electrical conductance and magnetism. The base material and the dopant forming a first region of housing 502 including a first skin depth and a second region of the housing including a second skin depth different than the first skin depth. For example, housing 502 includes annular region/portion 506, which has a first skin depth, and capped end regions/portions 508 and 510, which have a second skin depth. In one example, the second skin depth of ends 508 and 510 is "long" or greater than the first skin depth and is configured to propagate energy signals transmitted and/or received by antenna 504 and generally aligned with longitudinal axis 512 and coaxial field 518. Conversely, in an example, the first skin depth of annular region/portion 506 of antenna is "short" and is configured to attenuate energy signals aligned with axis 514 and coradial field 516 of antenna 504.

Figure 6:
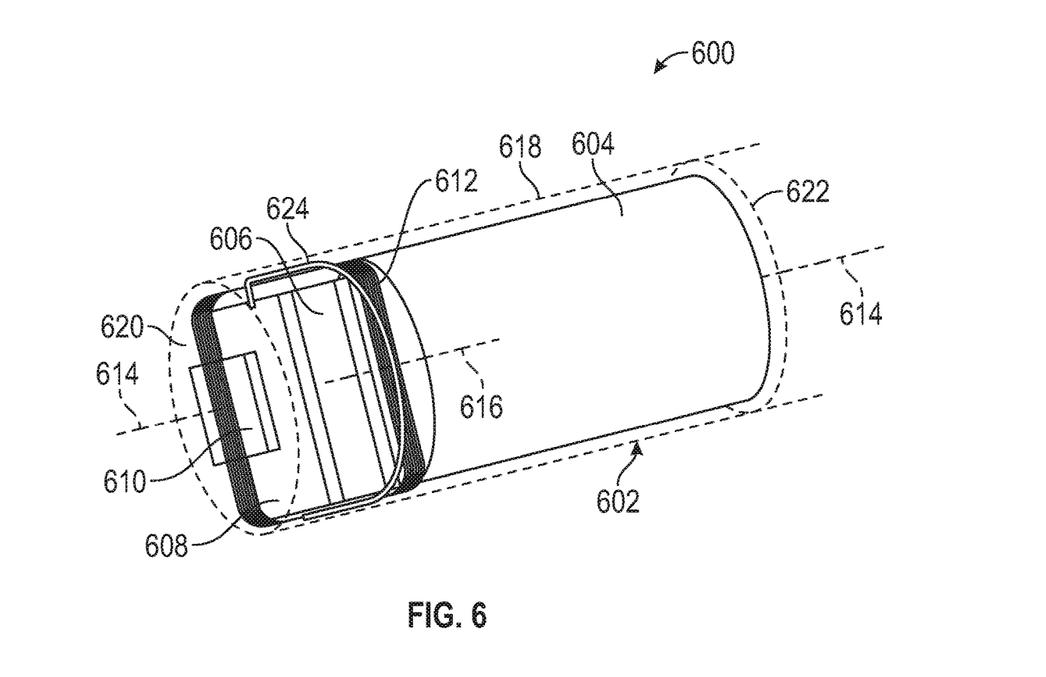
FIG. 6 is another example IMD including a heterogeneous housing.

FIG. 6 is another example IMD 600 including heterogeneous housing 602. IMD 600 may be what is sometimes referred to as a leadless pacemaker, leadless cardioverter defibrillator, or more generally a leadless electrical stimulation device. The volume of such IMDs is generally much less (e.g. 1% to 5%) than the volume of traditional implantable stimulators (for example, like the example IMD 102 of FIGS. 1 and 2) and are configured to be implanted with less invasive procedures and do not require running long leads through anatomy of the patient. The structure of such leadless IMDs may be similar to that of example IMD 602, including a generally cylindrical or capsule shaped housing with internal components arranged in multiple regions, including a battery region, electronics/circuit board region, and a suture or fixation region/mechanism for securing the IMD within a patient. In an example such leadless IMDs may be on the order of 10-15 mm long with a diameter on the order of 2-3 mm. In another example such leadless IMDs may be on the order of 20 to 40 mm long with a diameter on the order of 5 to 7 mm.

Example IMD 600 includes housing 602, battery 604, first PCB 606, second PCB 608, third PCB 610 and coiled antenna 612. Battery 604 can include a variety of batteries appropriate for the intended application of IMD 600 and is disposed in a first region within and may occupy a majority of the interior space of IMD 600. First, second and third PCBs 606, 608 and 610, respectively, are arranged within IMD 600 in a second region and are disposed such that vectors/axes normal to major surfaces of the PCBs are parallel to longitudinal axis 614 of housing 602. Antenna 612 is a coiled antenna that is disposed to surround PCBs 606, 608, and 610. Antenna 612 includes a rectilinear coil versus the curvilinear coil of antenna 504 of example IMD 500. Additionally, longitudinal axis 616 of antenna 612 is parallel to radii of cylindrical housing 602 and an axis normal to two sides of the outer periphery of the antenna is aligned with and parallel to longitudinal axis 614 of housing 602.

In examples, PCB 606 includes a storage and processing integrated circuit including components and functions for receiving and processing data and information including stimulation programs, sensor signals, among other examples, and for electrical pulse generation. PCB 608 can include, as an example, a Bluetooth or other wireless telemetry module, and PCB 610 can include a sensor PCB, including, for example, a pressure sensor module. The combination of processing, sensing, etc. modules included in the electronics of IMD 600 can vary depending upon the intended application of the device.

Housing 602 includes annular region/portion 618 and capped end regions/portions 620 and 622. Housing 602 is heterogeneous comprising an intrinsically non-conductive and non-magnetic base material and at least one dopant comprising at least one of electrical conductance and magnetism. The base material and the dopant forms at least a first region of housing 602 including a first skin depth and a second region of the housing including a second skin depth different than the first skin depth. For example, housing 602 includes annular region/portion 618, which has a first skin depth, and capped end regions/portions 620 and 622, which have a second skin depth. In one example, the first skin depth of annular region/portion 618 of housing 602 is "long" or greater than the second skin depth and is configured to propagate energy signals transmitted and/or received by antenna 612 and generally aligned with longitudinal axis 616 of antenna 612 and radii of housing 602. Conversely, in an example, the second skin depth of capped end regions/portions 620 and 622 of housing 602 are "short" and are configured to attenuate energy signals aligned with longitudinal axis 614 of housing 602 and vectors normal to two sides of rectilinearly coiled antenna 612. In this configuration, energy waves/signals (e.g., electromagnetic waves) aligned with long axis 614 of housing 602 may be attenuated to reduce interference or other undesirable effects on PCBs 606, 608 and 610, while energy waves/signals aligned with axis 616 of antenna 612 and radii of housing 602 may be propagated to allow receipt and transmission of power and/or signals (e.g., data) by antenna 612.

Coiled antenna 612 may be used for energy transfer and/or near field communication. IMD 600 may include a second non-coiled antenna 624 for far field communication. The operating frequency non-coiled antenna 624 may be different than that of coiled antenna 612. Coiled antenna 612 may reside inside, within or outside housing 602. Coiled antenna 612 may have an approximate omnidirectional radiation and reception pattern.

The foregoing examples include a heterogeneous IMD housing comprising an intrinsically non-conductive and non-magnetic base material and at least one dopant comprising at least one of electrical conductance and magnetic permeability, in which the base material and the dopant form two regions of the housing, each of which comprises a different skin depth. However, in other examples in accordance with this disclosure, an IMD housing can include more than two different regions, each of which includes a different skin depth. Additionally, in examples, a heterogeneous IMD housing can include two regions with the same first skin depth and a third region with a second skin depth that is different than the first skin depth. Additional combinations/variations of skin depth across different regions/portions of a heterogeneous IMD housing are also possible.

Additionally, properties other than skin depth can be varied across different regions/portions of heterogeneous IMD housings in accordance with this disclosure. For example, the rigidity/flexibility/resiliency of an IMD housing may be different in different regions of the housing. In other words, as an example, heterogeneous IMD housings in accordance with this disclosure may vary both electrical, e.g. skin depth, and mechanical, e.g., modulus of elasticity, across different regions of the housing. Increased flexibility in one region with greater rigidity and reduced flexibility in another region of an IMD housing may maintain the structural integrity of the housing while assisting in navigating to and implanting the IMD at a target site within a patient.

Example heterogeneous IMD housings in accordance with this disclosure can be made in a variety of ways employing a variety of manufacturing techniques, including various forming techniques like molding or casting, material removal techniques like milling, grinding, drilling, etc., and additive manufacturing techniques. Doping the intrinsically non-conductive and non-magnetic base material of heterogeneous IMDs can be accomplished by, for example, spraying and/or diffusion techniques/processes. In an example, a method of making a heterogeneous housing of an implantable medical device (IMD) includes forming the housing of the IMD from an intrinsically non-conductive and non-magnetic base material and at least one dopant comprising at least one of electrical conductance and magnetic permeability. In one example, forming the housing includes molding the heterogeneous IMD housing. The base material and the at least one dopant define a first region of the housing comprising a first skin depth and a second region of the housing comprising a second skin depth different than the first skin depth.

In some examples, the structure and contours of the finished housing may be formed from a combination of the base material and the at least one dopant and the distribution of the materials and/or ratio of base material to dopant in different regions may be controlled in situ as the housing (or parts thereof) are formed. In other examples, the housing may be formed up from only the base material to substantially the final shape and size, and then the at least one dopant may be applied to one or more portions/regions of the formed IMD. In some examples, the IMD housing may be produced in multiple pieces that are mechanically joined in some manner to produce a complete housing including multiple regions with multiple different characteristics/properties like different skin depths. In one example, an IMD housing in accordance with this disclosure includes a portion/region that is formed from a conductive metal and another portion/region that is formed from intrinsically non-conductive and non-magnetic polymer doped with at least one at least one dopant comprising at least one of electrical conductance and magnetic permeability, and the metallic and doped polymer portions/regions are mechanically or otherwise operatively coupled to one another.

Figure 7:
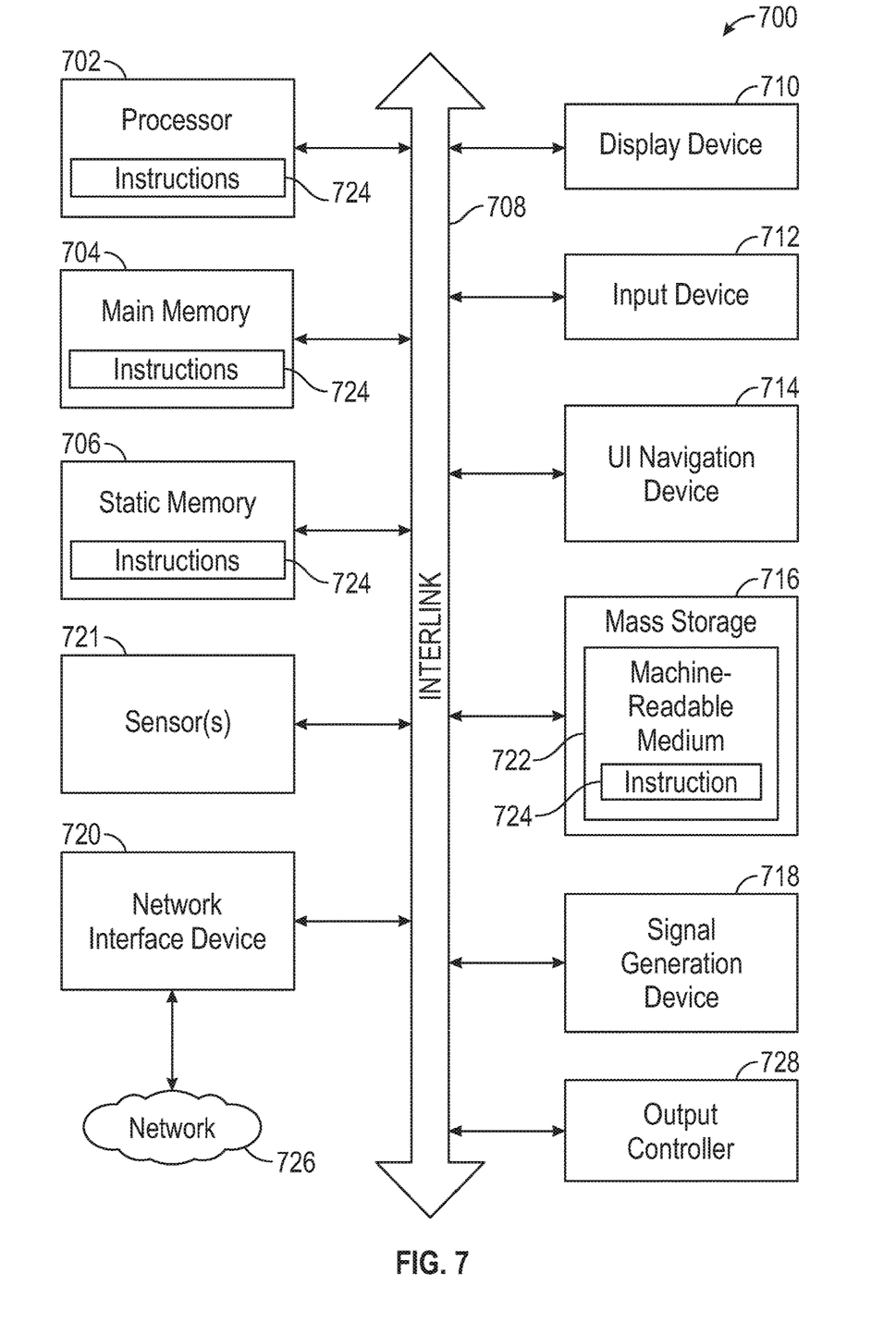
FIG. 7 illustrates a block diagram of an example machine upon which any one or more of the techniques (e.g., methodologies) discussed herein may perform.

FIG. 7 illustrates a block diagram of an example machine 700, the context in which any one or more of the techniques (e.g., methodologies) discussed herein may perform. The components of FIG. 7 (or any subset thereof) may be incorporated into a housing having a selectively varied skin depth. For example, some components (e.g., processor, main memory, static memory) may be selectively shielded from electromagnetic signals (e.g., noise) and some components (e.g., sensors, network interface device (e.g., antenna circuit)) may selectively placed proximate regions designed to propagate electromagnetic signals. Portions of this description may apply to the computing framework of various portions of the implantable medical device, such as implantable medical device 102 or the external system. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be or include a special purpose implantable or wearable device, personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable medical device (IMD) comprising:
   one or more electrical components; and
   a heterogeneous housing containing the one or more components of the IMD, the heterogeneous housing composed of:
      an intrinsically non-conductive and non-magnetic base material; and
      at least one dopant comprising at least one of electrical conductance and magnetic permeability,
   wherein the heterogeneous housing comprises:
      a first region of the housing having a first skin depth; and
      a second region of the housing having a second skin depth different than the first skin depth,
   wherein the different first and second skin depths of the first and second regions of the heterogeneous housing have different electromagnetic properties formed by the base material and the at least one dopant.

2. The IMD of claim 1, wherein the housing comprises a cylindrical housing with an elongated annular region and capped end regions.

3. The IMD of claim 2, wherein the first region comprises the elongated annular region and the second region comprises the capped end regions.

4. The IMD of claim 3, further comprising an antenna and a circuit board comprising two major surfaces disposed within the housing, and wherein:
   the first region of the housing is arranged in a path of electromagnetic waves received by and/or transmitted by the antenna;
   the second region of the housing is arranged in a path of electromagnetic waves normal to the major surfaces of the circuit boards; and
   the first skin depth is greater than the second skin depth.

5. The IMD of claim 3, further comprising an antenna and a circuit board comprising two major surfaces disposed within the housing, and wherein:
   the first region of the housing is arranged in a path of electromagnetic waves normal to the major surfaces of the circuit boards;
   the second region of the housing is arranged in a path of electromagnetic waves received by and/or transmitted by the antenna; and
   the first skin depth is less than the second skin depth.

6. The IMD of claim 1, wherein the housing has one or more low impedance paths between an internal component and an external lead port.

7. The IMD of claim 6, wherein the one or more low impedance paths comprise one or more feedthroughs.

8. The IMD of claim 1, wherein the base material is selected from the group consisting of polymers, ceramics, glasses, composites, metamaterials and combinations thereof.

9. The IMD of claim 1, wherein one of the first and second skin depths is approximately 10 mm at an operational frequency of the IMD.

10. The IMD of claim 1, wherein one of the first and second skin depths is approximately 1 mm at an operational frequency of the IMD.

11. The IMD of claim 1, wherein one of the first or the second skin depth is approximately 0.1 mm at an operational frequency of the IMD.

12. The IMD of claim 1, wherein one of the first and second regions of the heterogeneous housing propagates electromagnetic communication signals and the other of the first and second regions of the heterogeneous housing attenuates electromagnetic noise signals.

13. The IMD of claim 1, wherein the at least one dopant comprises a dopant having a target conductance and a target magnetic permeability that locally increase magnetic induction and skin depth of one of the first and second regions of the housing including the dopant relative to one or more other regions of the housing.

14. The IMD of claim 1, wherein one of the first and second regions comprises a rigid region and the other of the first and second regions comprises a flexible region.

15. The IMD of claim 1, wherein the dopant has a magnetism property and wherein the magnetism property comprises at least one of ferromagnetism, ferrimagnetism and anti-ferromagnetism.

16. The IMD of claim 1, wherein the one or more components comprise at least one antenna and another electrical component, and
wherein one of the first and second regions are configured to attenuate electromagnetic waves to the another electrical component and the other of the first and second regions are configured to propagate electromagnetic waves to the antenna.

17. The IMD of claim 1, wherein the first skin depth is greater than the second skin depth, the IMD further comprising an antenna disposed within the housing, and wherein the first region of the housing is arranged proximate the antenna to support propagation of electromagnetic waves to or from the antenna.

18. The IMD of claim 1, wherein the second skin depth is less than the first skin depth, the IMD further comprising a circuit board comprising two major surfaces, and wherein the second region of the housing is arranged in a path of electromagnetic waves normal to the major surfaces of the circuit boards, wherein the second region attenuates propagation of electromagnetic noise to the circuit board.

19. The IMD of claim 1, comprising:
a header or lead port connected to and separate from the heterogeneous housing.

20. A method of making a heterogeneous housing of an implantable medical device (IMD), the method comprising:
forming the heterogeneous housing of the IMD from an intrinsically non-conductive and non-magnetic base material and at least one dopant; and
varying the amount of dopant at first and second regions of the heterogeneous housing to provide a first skin depth at the first region of the housing and a second skin depth at the second region of the housing that is different than the first skin depth, wherein the different first and second skin depths of the first and second regions of the heterogeneous housing have different electromagnetic properties formed by the base material and the varying amount of dopant at the first and second regions.

* * * * *